(12) United States Patent
Iyer

(10) Patent No.: US 8,871,009 B2
(45) Date of Patent: Oct. 28, 2014

(54) SYSTEM FOR REMOVAL OF ORGANIC CONTAMINANTS FROM BIO-GAS FOR RENEWABLE ENERGY PRODUCTION

(75) Inventor: Subramanian Iyer, Yorba Linda, CA (US)

(73) Assignee: Subramanian Iyer, Yorba Linda, CA (US)

( * ) Notice: Subject to any disclaimer, the term of this patent is extended or adjusted under 35 U.S.C. 154(b) by 274 days.

(21) Appl. No.: 13/530,339

(22) Filed: Jun. 22, 2012

(65) Prior Publication Data

US 2013/0340616 A1 Dec. 26, 2013

(51) Int. Cl.
*B01D 53/14* (2006.01)

(52) U.S. Cl.
USPC .................................. 95/196; 95/205; 95/237

(58) Field of Classification Search
None
See application file for complete search history.

(56) References Cited

U.S. PATENT DOCUMENTS

| | | | |
|---|---|---|---|
| 2003/0178342 A1* | 9/2003 | Alexion et al. | 208/208 R |
| 2006/0204433 A1* | 9/2006 | Carrette et al. | 423/574.2 |

* cited by examiner

*Primary Examiner* — Duane Smith
*Assistant Examiner* — Pankti Patel
(74) *Attorney, Agent, or Firm* — Vito A. Canuso, III

(57) ABSTRACT

A method of reducing siloxane contamination in an effluent gas is described, where one embodiment of the method comprises directing the effluent through a reactor comprising a dialkyl terminated glyme solvent having a molecular size less than about 300 Daltons, the dialkyl terminated glyme serving to physically absorb the siloxanes from the effluent; polymerizing the siloxanes by directing them through a packed bed of acidic resin catalyst media housed within the reactor and immersed within the solvent so as to create polymerized siloxanes having a molecular size greater than about 300 Daltons, that are soluble in the solvent; and separating the polymerized siloxanes from the solvent via nanofiltration; and recycling the solvent into the reactor for further physical absorption of incoming siloxanes.

4 Claims, 3 Drawing Sheets

SYSTEM FOR REMOVAL OF ORGANIC CONTAMINANTS FROM BIO-GAS FOR RENEWABLE ENERGY PRODUCTION

FIELD OF THE INVENTION

The embodiments herein relate generally to a system for removing contaminants from effluent and discharge gas flows and, more specifically, to the removal of siloxanes and the like from such flows. Similar technologies can be adopted for removal of other polymerizable contaminants from gas flows, like hydrogen sulfide and other organic sulfides from bio-gas or natural gas streams, using appropriate solvents and catalysts.

BACKGROUND

Landfills and sewage treatment plants contain siloxanes from many sources, both industrial and domestic. One source of siloxanes is the semiconductor industry, which produces siloxanes as by-products of reactions involving silicon compound gases. Because siloxanes have detrimental effects on semiconductor products, siloxanes are removed from semiconductor process gases by processes such as adsorption onto diatomaceous earth, silica gel, molecular sieves, activated carbon or activated alumina.

The personal care industry uses volatile methyl siloxanes in products such as deodorants, tooth-pastes, skin care preparations, hair conditioners and anti-perspirants.

The cleaning industry finds many applications for siloxanes. In dry cleaning, siloxanes are used as a more environmentally friendly solvent than traditional chlorofluorocarbons. In the electronics industry, siloxanes are used to clean circuitry.

Siloxane-containing waste from industrial and domestic sources is discharged into landfill sites and sewage treatment plants, along with a variety of biological organic matter. The organic matter in the waste decomposes to produce bio-gas containing various volatile organic compounds, such as methane. The bio-gas can be used to fuel various combustion engines to produce power, or both heat and power. However, the bio-gas from landfill sites and sewage treatment plants is contaminated with siloxanes. When an engine burns siloxane-contaminated bio-gas, the siloxanes, on oxidation, forms precipitates of silicon dioxide. The precipitates are deposited on engine parts such as turbine blades, pistons, cylinders, heat exchangers and emission control equipment. The deposits increase the abrasion of engine surfaces, leading to a loss of engine efficiency and premature engine failure. The deposits also poison catalytic converters in emission control equipment.

According to the EPA's most recent data (2007), the U.S. has over 1,700 active landfills. Though the number of landfills has significantly decreased over the last 20 years, the average size of landfills has increased. Landfill sites produce methane and carbon dioxide gases due to the natural decomposition of solid waste material. Solid waste landfills are the second largest source of human-related methane emissions in the United States, accounting for approximately 23 percent of these emissions in 2007. In fact, these methane emissions from landfills represent a lost opportunity to capture and use a significant energy resource. Instead of allowing landfill gas (LFG) to escape into the air, it can be captured, converted, and used as an energy source. Financial benefits and improved community relations now provide the landfill industry with multiple incentives to employ bio-gas conditioning systems in the management of these gases.

Similarly, approximately 14,000 wastewater treatment facilities (WWTFs) operate in the United States, ranging in capacity from several hundred million gallons per day (MGD) to less than 1 MGD. Roughly 1,000 of these facilities operate with a total influent flow rate greater than 5 MGD, but only 544 of these facilities employ anaerobic digestion to process the wastewater. Moreover, only 106 WWTFs utilize the bio-gas produced by their anaerobic digesters to generate electricity and/or thermal energy. If the remaining WWTFs were to install combined heat and power technologies, approximately 340 MW of clean electricity could be generated, offsetting 2.3 million metric tons of carbon dioxide emissions annually. These reductions are equivalent to planting approximately 640,000 acres of forest, or the emissions of approximately 430,000 cars.

Utilization of bio-gas conditioning systems provides landfills and WWTFs with an opportunity to collect and dispose of the high levels of methane found in landfill and WWTF digester gases. Currently, many landfills and WWTFs are using untreated gas containing impurities such as sulfur, chlorine, silicon and moisture, to generate power and fire boilers. This untreated gas can make existing equipment such as boilers, engines, fuel cells and turbines susceptible to increased damages, increased maintenance costs and shorter life spans.

Siloxane concentrations are generally higher in digester gas than in landfill gas. Table 1 shows the various siloxanes encountered in bio-gas facilities. Siloxanes in digester gas appear to be predominantly $D_4$ and $D_5$, while landfill gas may additionally contain other siloxane compounds, like $D_3$ and $D_6$, as well as $L_2$ through $L_5$. In addition, significant quantities of trimethyl silanol can also be present in these gas streams.

TABLE 1

| Name | Formula | Abbreviations | Molecular Weight (gm/mole) | Vapor Pressure at 25° C. (mm Hg) |
| --- | --- | --- | --- | --- |
| Hexamethylcyclotrisiloxane | $C_6H_{18}O_3Si_3$ | $D_3$ | 222 | 10 |
| Octamethylcyclotetrasiloxane | $C_8H_{24}O_4Si_4$ | $D_4$ | 297 | 1.3 |
| Decamethylcyclopentasiloxane | $C_{10}H_{30}O_5Si_5$ | $D_5$ | 371 | 0.4 |
| Dodecamethylcyclohexasiloxane | $C_{12}H_{36}O_6Si_6$ | $D_6$ | 445 | 0.02 |
| Hexamethyldisiloxane | $C_6H_{18}Si_2O$ | MM, $L_2$ | 162 | 31 |
| Octamethyltrisiloxane | $C_8H_{24}Si_3O_2$ | MDM, $L_3$ | 236 | 3.9 |
| Decamethyltetrasiloxane | $C_{10}H_{30}Si_4O_3$ | $MD_2M$, $L_4$ | 310 | 0.55 |
| Dodecamethylpentasiloxane | $C_{12}H_{36}Si_5O_4$ | $MD_3M$, $L_5$ | 384 | 0.07 |

The landfill gas and wastewater digester gas industries, when generating power, have been dealing with the impact of siloxane build up for years. Increased equipment maintenance and replacement costs due to siloxanes from wastewater digester gas systems and landfill gas systems were assumed to be standard operating issues that each plant was forced to incorporate into their operating budgets. Attempts to minimize environmental pollution, specifically $NO_x$ reduction technologies, such as selective catalytic reduction to reduce air emissions from bio-gas fueled equipment, often resulted in failure of the catalyst after a few days due to the presence of siloxanes, with the catalyst surfaces getting coated with a thin layer of silicon dioxide and thereby rendered inactive. Biogas with siloxanes higher than 50 parts per billion by volume (ppbv) can cause significant damage to gas turbine power generation equipment. Levels higher than 100 ppbv may also damage internal combustion engines. The proper treatment of input gas using bio-gas purification technologies needs to remove siloxanes to levels of less than 10 ppbv.

Allowable siloxane contents for various power generation turbine systems are shown in Table 2, below, as obtained from various turbine manufacturers. Typical landfill gas siloxane contents range around 20-35 $mg/m^3$, and thus are much higher than allowable limits in most turbine fuel specifications.

TABLE 2

| Turbine manufacturers | Si limits in $mg/m^3$ |
| --- | --- |
| Capstone Turbines | 0.03 (5 ppbv) |
| Solar Turbines | 0.1 (16.7 ppbv) |
| Ingersoll Rand (FlexFuel) | 0.06 (10 ppbv) |
| GE Jenbacher | 10 |
| GE Waukesha | 25 |
| Deutz | 5 |
| Caterpillar Turbines | 28 |

Siloxane removal systems have historically taken the form of chilling or adsorption/absorption. Some systems incorporate moisture control with chilling to $-7°$ C., essentially to remove the volatile siloxanes by manipulation of their dew points. The most widely used method to reduce siloxane concentrations is adsorption on activated carbon (or activated alumina). Depending on the activated carbon, overall silicon reduction of up to 98% is possible. Since bio-gas contains a broad range of different compound classes with concentrations varying over several orders of magnitude, competitive adsorption of contaminants occurs. The presence of relatively non-volatile, sulfur-containing or halogenated compounds, for example, can greatly reduce the adsorption capacity of the activated carbon towards siloxanes. Other factors influencing the siloxane adsorption capacity of activated carbon are the relative concentrations of the siloxane species to one another, alas well as temperature and relative humidity. Similarly, activated alumina can also be used for siloxane adsorption. Regeneration of the adsorption media is accomplished by passing hot, inert gases through the media to desorb the siloxanes and vent them into the atmosphere. Siloxanes are not considered volatile organic compounds (VOCs), and thus can be discharged into the atmosphere, where they oxidize with atmospheric oxygen to silicon dioxide over time.

Sites such as the Toland Road Landfill in Santa Paula, Calif., require a monthly change of the activated carbon, once saturated with organic and other contaminants. The cost for regeneration of activated carbon adsorbents is approximately $10,000 per change at the Toland Landfill Site. Regenerating activated alumina is cheaper than regenerating activated carbon, though the initial costs of activated alumina are higher.

Absorption technologies are another pathway for siloxane removal. Physical and chemical absorption can be distinguished. In theory, the latter is applicable to siloxane elimination, as the siloxanes are destroyed by strong bases and acids at high or low pH-values, respectively. However, the potential application of these chemical absorption agents is associated with high costs, safety and corrosion issues, and therefore has not been adopted widely. Moreover, only acidic liquids can be used for bio-gas facilities, unless carbon dioxide is removed upstream of the siloxane removal system for fuel gas upgrading, as bases react with the carbon dioxide in the bio-gas to form carbonates, which in turn precipitate onto the equipment. Among the most effective acidic solutions are nitric acid (>65%) and sulfuric acid (>48%), which remove many species by over 95%. This is only possible at temperatures above 60° C., while elimination at 20° C. is noticeably lower.

The second type of absorption is physical, including absorbents such as water, organic solvents or mineral oil. The absorption of volatile methyl siloxanes (VMS), most of which are hydrophobic, in water (at pH 7) was not proven to be very successful; nevertheless, some water-soluble contaminants including trimethylsilanol and hydrogen sulfide could be removed. Absorption using water is therefore a common pre-conditioning step to enhance the effectiveness of subsequent adsorption by activated carbon. Absorption with liquid solvents like 'SELEXOL' (essentially composed of polyethylene glycol dimethyl ether, PEGDME) from Dow Chemicals has also been used for removal of siloxanes, though the solvent is primarily used for removal of acidic gases like carbon dioxide, hydrogen sulfide, COS and mercaptans. These species dissolve appreciably in the solvent before the siloxanes are solvated. Regeneration of SELEXOL is accomplished by scrubbing the solvent with hot inert gases or by exposure to high temperatures, whereby the contaminants volatilize out, and leave the solvent behind for reuse and recycling into the liquid scrubbing system. There are many different liquid chemicals that are able to preferentially absorb contaminants from landfill gas. An absorption column could be designed around any one of these chemicals and the result would be efficient removal of siloxane contaminants. The problem with physical absorption is that once the absorption media reaches saturation, regeneration is required. This can be cost prohibitive in the case of the aforementioned liquid absorbents, if done using traditional methods like subsequent vaporization of the volatile contaminants. Water is not a suitable solvent for most siloxane compounds. Many different organic compounds such as methanol and ethanol also do not function quite well as siloxane solvents. Most siloxanes are non-polar compounds, and hence the use of polar solvents like water, methanol and ethanol, or glycols like ethylene glycols and propylene glycols, provides insufficient solvation of the siloxane species, rendering them unsuitable for dissolving the siloxanes for subsequent removal or sequestration.

Another known technique is condensation of the volatile siloxanes under high pressure but low temperatures. However, mere cooling to temperatures around 5° C. has proven to be unsuitable for quantitative VMS removal. The removal efficiency achieved by deep chilling depends on the respective siloxane concentrations in the raw gas. The more volatile the siloxane moiety, the more difficult it is to condense; certain troublesome species can practically not be reduced to concentrations lower than present in bio-gas. In order to reach higher removal efficiencies, condensation could theoretically be performed at higher pressures. Attainable siloxane concentrations decrease by the same factor as the operating pressure is increased. It is clear that the lower the siloxane load of the raw gas, the more difficult it is to remove siloxanes. A landfill gas with silicon concentrations of 50 mgSi/m3 must be chilled to −30° C. to reach a removal efficiency of roughly 50%, while −40° C. would remove roughly 70%. Still lower temperatures do not lead to any more significant purification, as the remaining siloxanes do not condense noticeably. Only at unusually high siloxane loads and very low sub-zero temperatures does condensation of these species commence. Due to relatively high investment and operating costs, deep chilling is generally regarded as economically suitable only at high gas flow rates and elevated siloxane load. In addition, the process is also subject to problems of ice formation of any contaminating water present. New siloxane removal methods being investigated include temperature swing absorption (TSA) or pressure swing absorption (PSA), whereby temperatures and pressures, or both, are manipulated, along with use of adsorbents, to remove the volatile organics by simultaneous condensation and adsorption.

One method currently being investigated is the use of gas separation membranes. This implies the principle of selective siloxane permeation by solution and diffusion through dense polymeric membrane materials. Ideally, the product component methane needs be retained as much as possible and should not pass through the membrane. Hybrid membranes comprised on polydimethylsiloxane (PDMS) and zeolites have been proposed in literature, though VMS cleanup has not been very successful.

Thus, previous attempts at removing siloxane contaminants from bio-gas have used adsorbents such as activated charcoal, activated alumina, molecular sieves and silica gel, or chilling and refrigeration techniques to condense and separate the volatile siloxanes from bio-gas. However, none of these techniques are able to clean up siloxane contamination at low costs. Improved techniques for removing siloxanes from bio-gas are thus needed, but has eluded persons of ordinary skill in the art. The present invention solves this problem, as described below.

SUMMARY

In embodiments of the present invention, a novel method is described to scrub organic contaminants like siloxanes from bio-gas collected from, for example, landfill sites and wastewater treatment facilities, by using physical absorption in special liquid solvents and in situ polymerization, by special solid-state catalysts, of the dissolved volatile, low-molecular-weight siloxanes into higher molecular weight organosiloxanes or polydimethylsiloxanes (PDMS). The contaminant-saturated liquids are subsequently regenerated and recycled back into the system by filtration through a special solvent-stable nano-filtration membrane, enabling the higher molecular weight polymerization products to be filtered out, while the liquid solvents are recycled back into the liquid scrubbing system.

One embodiment of the present invention comprises a three-phase heterogeneous process: between a packed bed of solid siloxane polymerization catalysts, gaseous siloxane contaminants carried along with the bio-gas, and a liquid solvent to preferentially solvate the contaminant siloxanes as well as their polymerization products from the catalyst bed for subsequent sequestration. This results in a simplified low-energy pathway to clean up the bio-gas from siloxane contaminants, with the siloxanes being separated from the bio-gas, sequestered as liquid polymerization products, and separated by special filtration techniques for subsequent disposal.

BRIEF DESCRIPTION OF THE FIGURES

The detailed description of some embodiments of the invention is made below with reference to the accompanying figures, wherein like numerals represent corresponding parts of the figures.

DETAILED DESCRIPTION OF CERTAIN EMBODIMENTS

Figure 1:
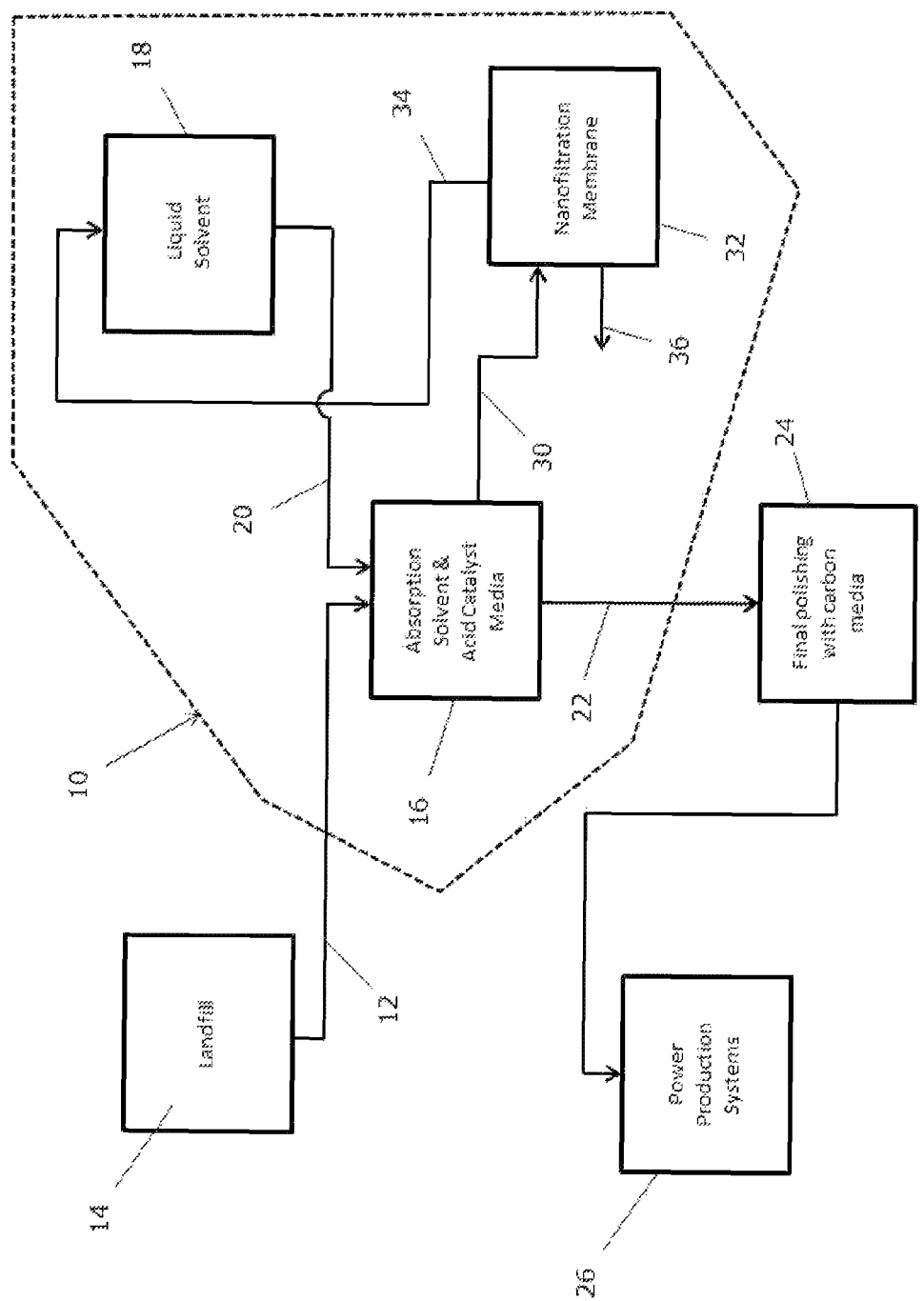
FIG. 1 is a schematic of one embodiment of a reactor system of the present invention as applied to landfill effluent gas containing contaminants to be removed.

Embodiments of the present invention comprise one or more of three otherwise distinct processes employed in unique arrangements to scrub contaminants from hydrocarbon effluent gases (bio-gas) that results in enhanced and useful energy generation from the effluent gases. In certain embodiments, the three processes comprise absorption using a liquid medium, polymerization using a solid catalyst and separation using filtration. Variations on each are contemplated, however, including the phase of the media and/or catalyst and the type of filtration or separation mechanism.

With regard to the process of absorption, while solid-phase or gas-phase scrubbing can be effective, it is preferred that a liquid-phase solvent be employed; i.e., liquid at standard temperature and pressure. The preferred solvent should have a high boiling point, preferably in excess of 200° C., and appreciably low vapor pressures, to minimize loss of the liquid solvent during gas scrubbing operations. Where the contaminant at issue is siloxane (see, for example, Table 1 above), the solvent should exhibit high siloxane solvation tendencies, resistance to peroxide formation, and chemical resistance to degradation or polymerization in acidic or basic environments. The preferred solvent should be a low molecular weight liquid because nanofiltration membranes separate liquid components based upon molecular weight and size constraints, typically allowing permeation of molecules of size lesser than 300 Daltons (Da), but retaining larger molecules.

In certain embodiments of the invention, the absorption solvent comprises an organic liquids having a molecular weight of less than 300 Daltons, with inherent chemical stability towards catalysts, acids and bases, to physically absorb the organic contaminants at issue. In the case of siloxanes, certain ethers comprising dialkyl terminated glymes are preferred, including butyl diglyme (diethylene glycol dibutyl ether), ethyl glymes, ethyl diglymes, triglyme and tetraglyme, hexyl ether, anisole, dibenzyl ether, but also polyethylene glycols and propylene glycols are contemplated, as well as compounds such as butyl glycol ether acetates or methoxy propyl acetates (also known as propylene glycol methyl ether). With the latter two solvents, a propensity for peroxide formation over time may be inhibited with agents like 2,6-di-tert-butyl-para-cresol (2,6-BHT). Those compounds with acetate groups at their ends may render the solvents prone to polymerization themselves in acidic or basic environments. Similarly, solvents with hydroxyl groups at their ends are less suitable, because the hydroxyl groups render them prone to polymerization themselves in acidic or basic media.

A preferred solvent, butyl diglyme, is end-capped with butyl groups, and unlike other methyl end-capped glymes, is not miscible with water. The high flash point of butyl diglyme renders it safe for use in industrial applications, and it is not generally considered a volatile organic compound (VOC), thus providing an environmentally friendly solvent. Its boiling point is 256° C., while its water solubility is only 0.3 mg/liter. Butyl diglyme is stable in both acidic and basic environments. Similar solvents, like tetraethylene glycol dimethyl ether, polyethylene glycol dimethyl ether or dipropylene glycol dimethyl ether, can also be used for the purposes described herein, though their water miscibility is higher than for butyl diglyme. These glyme solvents have no free hydroxyl functionality, and thus are exceedingly stable in polymerization reactions, acting both as carrier molecules, as well as phase-transfer catalysts. A mixture of glymes may also be used, particularly where both polar and non-polar siloxane contaminants exist in the bio-gas, depending on the concentration of each.

Recognizing the regeneration of the solvent is desirably from an energy efficiency standpoint, and contemplating filtration as one means of achieving separation of the solvent for recirculation, it is contemplated that an inventive combination with the absorption process is to polymerize the contaminants, such as the siloxanes, so that during filtration, the liquid solvent employed may be separated from the solubilized and polymerized contaminants due to the larger molecular size of the contaminants. Any component that is too large in size will not pass through the membrane of a filter, such as polymerized siloxane contaminants. In that regard, significant research effort was spent evaluating various candidates of solvents to find those that dissolved contaminants such as siloxanes (having a range of polarities), were non-volatile, were of small-enough molecular size to pass through filtration for purposes of regeneration, did not inhibit polymerization of the contaminants, and did not degrade on the presence of the polymerizing catalyst.

Embodiments of the invention preferably comprise the use of acidic polymerizing catalyst. As both landfill gas and wastewater digester gas are significantly contaminated with carbon dioxide, use of basic catalysts would lead to catalyst degradation or poisoning, due to formation of basic carbonate salts. Acid-catalyzed condensation of silanol and silyl ether groups is an important reaction leading to the formation of the siloxane bond. With cyclosiloxanes, the monomer ring is involved in both the initiation and the propagation steps of polymerization. Ring-opening polymerization is a form of chain-growth polymerization, in which the terminal ends of a polymer acts as a reactive center, where further cyclic monomers join to form a larger polymer through ionic propagation.

The treatment of some cyclic compounds with catalysts brings about cleavage of the ring, followed by polymerization to yield higher molecular-weight entities. Similarly, linear siloxanes can be added to the chain by redistribution polymerization techniques. Thus, both cyclic siloxanes and linear siloxanes can be polymerized to polyorganosiloxanes by ring-opening polymerization and/or redistribution polymerization. The polymerization can be carried out by the anionic route, via basic catalysts, or the cationic route, via acid catalysts.

It is preferable to use solid-state or non-volatile liquid acid catalysts, via the cationic route, as they enable easier separation of the catalysts from the liquid solvents and the solvated siloxane molecules. The use of a solid-state catalyst packed bed also increases the probability of several siloxane molecules coming into contact with each other for polymerization to occur, due to the higher concentration of these molecules in the densely-packed catalyst bed.

The strongly acidic family of sulfonic and phosphonic acid compounds are readily available, proven to polymerize volatile siloxane monomers to nonvolatile oligomers and polymers, and are available commercially as polymer-bound resins. In particular, sulfonic acid, like sodium polystyrene sulfonate, or phosphonic acid resin-based solid-state catalysts are preferred for polymerization of the siloxanes to high molecular-weight silicone polymers like organosiloxanes or PDMS. One example of a suitable acidic resin catalyst is Monosphere® M-31 ion exchange resin by Dowex®, where the sodium ions have been replaced by $H^+$ ions. These are strongly acidic cation exchange resins, with a wet volume capacity, in the H form, of 1.91 meq/mL and a mean particle size of 500 microns. The [—SO3H] groups are fixed on a solid support, and thus cannot move around as in homogeneous media. The use of such solid acid catalyst resins, with a liquid solvent for sequestering and polymerizing volatile siloxanes in landfill or digester gas, results in a three-phase reaction volume of solid-liquid-gas interaction in the proposed invention.

Regeneration of the liquid solvent is advantageous for the techno-economic viability of siloxane removal. One cost effective means for the separation of low molecular weight liquid solvents from higher molecular weight siloxane solutes is nanofiltration (NF), using solvent-stable membranes, which are capable of filtering out molecules with a size greater than 300 Daltons (Da), a cutoff size greater than the molecular size of the solvent itself. It is contemplated that other filtration-separation systems may be employed depending upon the solvent media and polymerization catalyst, including ultrafiltration, reverse osmosis, and forward osmosis, among other systems. In the case of a siloxane removal embodiment employing, for example, butyl glyme as the solvent, NF purification and regeneration of the liquid absorbent is preferably the low-energy pathway. The use of solid-state catalysts advantageously avoids interfering or destabilizing the membranes used in nanofiltration, although liquid-phase polymerization catalysts may also be employed if the membrane materials are inert to them.

With regard to the NF embodiments, it is preferred that a membrane comprising a molecular weight cutoff of 300 Da be employed so that smaller molecular weight siloxanes are not filtered out or separated from the solvent. These unseparated siloxanes may preferentially serve as seed molecules for polymerization to occur in the packed bed catalysts, as described earlier.

Referring to FIG. 1, application of one embodiment 10 of the present invention to bio-gas may be appreciated. In that regard, in the context of treating, for example, landfill (effluent) bio-gas 12 from a landfill 14 (or wastewater treatment plant), embodiment 10 comprises a system 16 for absorbing siloxane contaminants in the landfill gas 12 and polymerizing the siloxane contaminants. Solvent 18 is provided to system 16 via delivery line 20. One embodiment of the invention comprises a solvent from the group consisting of butyl diglyme or other similar glymes or other non-protic solvents capable of dissolving linear and cyclic siloxanes, and more preferably, solvents from the family of dialkyl terminated glymes. The reactor is configured to permit a suitable physical interaction between the solvent and the effluent landfill gas discharge from the landfill, which includes contaminated organic material that should be removed prior to use in power generation equipment. The landfill effluent gas may be directed into reactor 16 under high pressure, so the reactor is preferably configured to withstand high pressures.

In one embodiment, the invention comprises reactor 16 housing the organic solvent flowing through solid state acidic catalyst to permit interaction between the solvent, the solid state catalyst media and any contaminants within the effluent gas. The treated effluent gas 22 discharged from reactor 16 may be directed for further processing (e.g., passing through an activated carbon filter 24) or for release into the inlet of downstream power generation equipment 26. For purposes of regenerating the liquid solvent, one embodiment of the present invention further comprises discharge line 30 from reactor 16 containing the solvent and absorbed or dissolved polymerized siloxanes, which is directed to a means for separating the solvent from the polymerized siloxanes, such as a nanofiltration system 32. The separated solvent 34 may then be directed to the solvent supply 18 for supply to reactor 16 as needed. The polymerized contaminants 36 separated by the nanofiltration system 32 may be disposed in any fashion desired.

Figure 2:
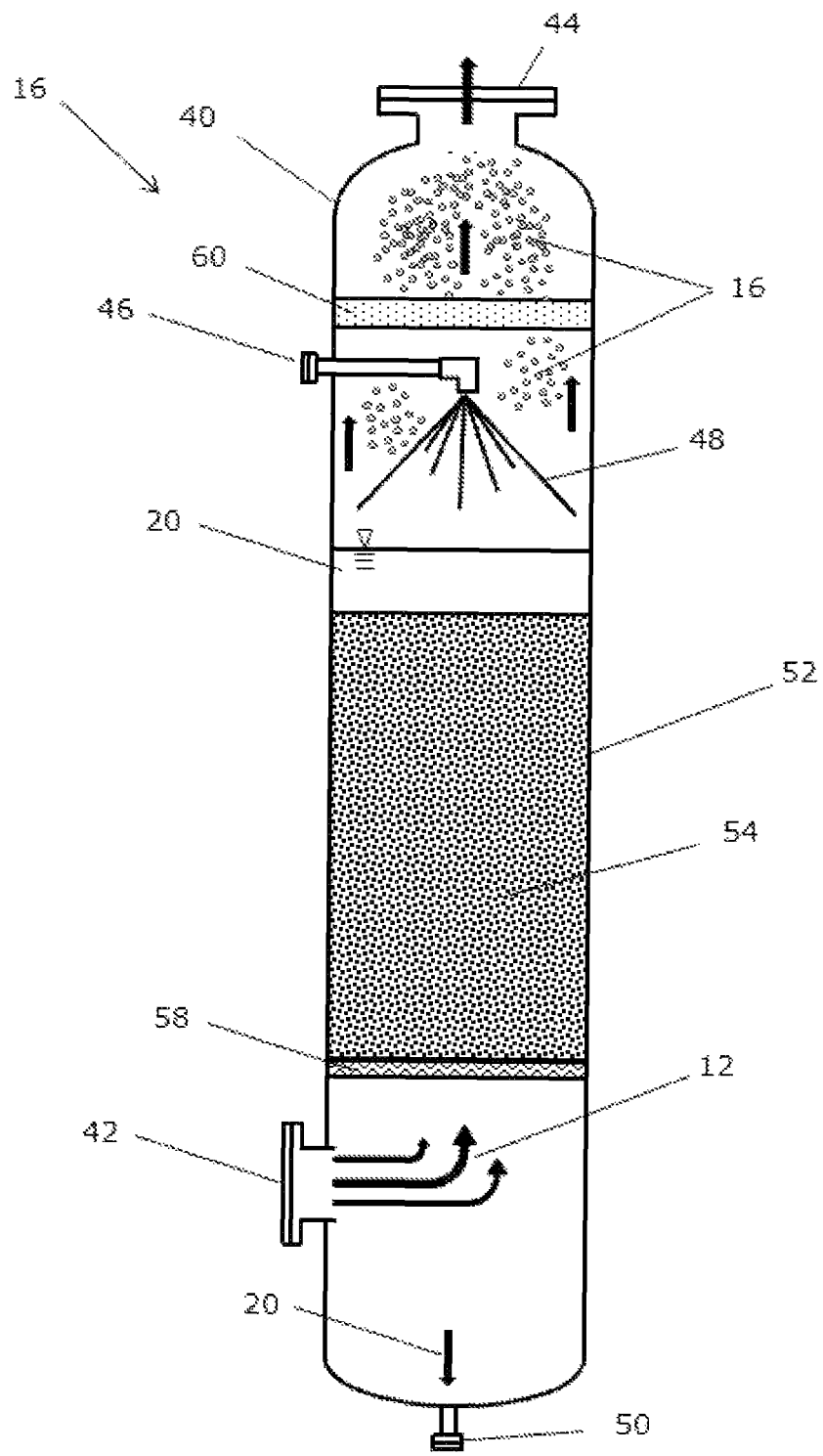
FIG. 2 is a schematic of one embodiment of a reactor in a reactor system of the present invention.

Referring to FIG. 2, one embodiment of the present reactor may be described. In that regard, reactor 16 comprises a housing 40, preferably a high pressure housing in case effluent gas is delivered above ambient pressure. The reactor housing 40 comprises an inlet 42 for the introduction of effluent gas 12 from, for example, the landfill, and an outlet 44 for the discharge of treated effluent gas for further treatment or to power production systems (see FIG. 1). Housing 40 further comprises an inlet 46 for the introduction of solvent 20 from the solvent supply 18 (FIG. 1). The solvent 20 is preferably sprayed 48 into the interior of the reactor housing 40 to enhance contact with the effluent gas, as explained further below. The reactor housing 40 further comprises an outlet 50 for the circulation of solvent and polymerized contaminants to the separation mechanism, such as the nanofiltration system 32 (FIG. 1).

In a preferred embodiment of reactor 16, a packed bed 52 of polymerizing catalyst 54 is supported above a mesh support 58 within the reactor housing 40, which further comprises a mesh 60 above the solvent inlet 46 to preclude the inadvertent discharge of polymerizing catalyst 54 from the reactor 16. In one application of the reactor 16 for treating siloxanes, the polymerizing catalyst 54 comprises a packed bed of Monosphere® M-31 ion exchange resin, which is fully immersed in the solvent 20, which preferably comprises a dialkyl terminated glyme, such as butyl diglyme, introduced into the reactor 16 at inlet 46. In operation, the effluent gas from the landfill is introduced at inlet 42 and directed upwardly through the packed bed of polymerizing catalyst 54 and bubbles upwardly 64 above the introduction of sprayed solvent 48, through mesh 60, and out through outlet 44 at the top of the reactor 16. The solvent 20 is sprayed 48 for thorough dispersion among the polymerizing media for interaction with the effluent gas passing through it in a counter-current passage, relative to the solvent used. The solvent 20 is re-circulated to replenish the reactor through outlet 50 at the base of the reactor 50. It should be noted that an embodiment of the reactor may house the catalyst media so that it is wetted by the solvent within the reactor.

Figure 3:
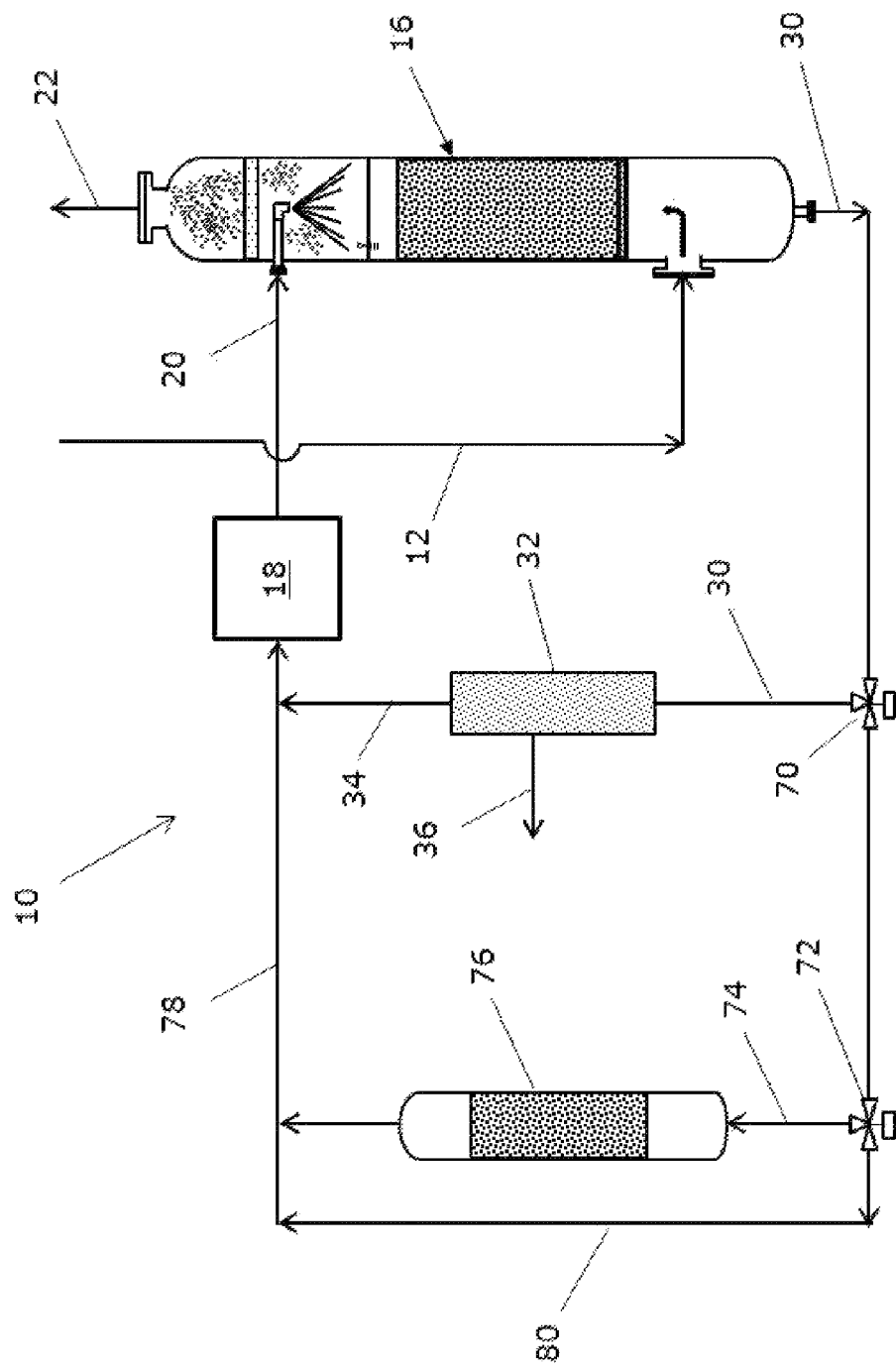
FIG. 3 is a schematic of one embodiment of a reactor system.

Referring to FIG. 3, a variation on one embodiment 10 of the present invention may be described. As described at a high level in FIG. 1, the reactor 16 processes effluent gas 12 for discharge 22 for further treatment or for use in power production. The solvent 20 is introduced into the reactor 16 from solvent supply 18, and then combined solvent and polymerized siloxane 30 is directed to nanofiltration system 32 for regeneration 34 back to either solvent supply 18 or directly to reactor 16. It is contemplated that a valve system 70 may be provided within embodiment system 10 to direct some of the combined solvent and polymerized siloxane 30 into the nanofiltration system, while directing some of the combined solvent and polymerized siloxane 30 through second valve system 72 and through inlet 74 into a second packed bed reactor 76 of polymerizing catalyst, the outlet of which 78 may be directed to either solvent supply 18 or directly to reactor 16. It is contemplated that further polymerizing of the siloxanes may act as a seed for the reaction taking place within the packed bed of catalyst within main reactor 16. If so desired, a third parallel flow line 80 may be provided so that the combined solvent and polymerized siloxane 30 may skip both the nanofiltration system 32 and the secondary reactor 76 if so desired, for flow to either solvent supply 18 or directly to reactor 16.

Experiments were performed to assess the effectiveness of siloxane polymerization, when landfill gas was passed though a packed bed of Monosphere® M-31 ion exchange resin, immersed in a liquid column of butyl diglyme. Initial siloxane contents and final siloxane contents were measured from the inlet gas and the gas outlet. Testing of the liquid solvent, after passing the landfill gas, with and without the catalyst acid media, by gas chromatograph mass spectrometry, showed a distinct speciation of siloxanes towards higher molecular weights, indicating that polymerization of the siloxanes had occurred with the catalyst.

Referring to Tables 3 and 4 below, certain siloxane removal results are shown. Table 3 specifically shows the results of siloxane removal using various solvents, gradually moving left-to-right from polar to non-polar solvents. Beginning with an inlet gas siloxane level of 19.81 ppmv, the solvents reduced the siloxane level (through absorption) from as high as 14.26 to 3.08 ppmv.

TABLE 3

| Test Conditions | | | | |
|---|---|---|---|---|
| Scrubbing system height: 55" Solvent used: as indicated below Landfill gas pressure: 103 psi | | | Scrubbing system diameter: 6" Solvent volume used: 4.0 liters Landfill gas volume passed: 500 SCF | |
| Inlet gas (Siloxane, ppmv) | Outlet gas, solvent = Ethylene glycol | Outlet gas, solvent = Ethylene glycol:propylene glycol (50:50) | Outlet gas, solvent = Methoxy propyl acetate | Outlet gas, solvent = Butyl diglyme |
| 19.81 | 14.26 | 12.72 | 4.88 | 3.08 |

Table 4 shows the effects of the solvent and the catalyst working simultaneously. Use of both the solvent and the polymerization catalyst, can remove siloxanes from landfill gas by a factor of 22-30, even when the solvent was not fresh, or regenerated and cycled. Thus the use of the described invention, upstream of a carbon-media adsorption column, would be able to reduce the final siloxane concentration, after the carbon bed, to a level lower than 0.1 ppmv, as required by several micro-turbine manufacturers' specifications for power generation from bio-gas from landfill sites and WWTF digester gas plants.

TABLE 4

| Test Conditions | | | | |
|---|---|---|---|---|
| Catalyst bed height: 3" Solvent used: Butyl Diglyme Landfill gas pressure: 103 psi | | | Catalyst bed diameter: 5.9" Solvent volume used: 4.0 gallons Landfill gas volume passed: 500 SCF | |
| Inlet gas (Siloxane, ppmv) | Outlet gas, fresh solvent, no catalyst | Outlet gas, initial scrubbing, solvent with catalyst | Outlet gas, 250 SCF scrubbed, solvent with catalyst | Outlet gas, 500 SCF scrubbed, solvent with catalyst |
| 19.81 | 3.08 | 0.46 | 0.63 | 0.87 |

The glyme solvent was subsequently subjected to nanofiltration, using a special solvent-stable membrane, obtained from SolSep BV, Netherlands. The membrane used was a 2.5" diameter, 40" length, NF membrane of the specification NF080105, SR2. Pressures used were 150 psi, and almost all the solvent was recovered, with a small volume retained by the membrane, containing the contaminating polymerized siloxanes. The molecular weight cutoff (MWCO) of the NF membrane was 300 Daltons. Only siloxanes of smaller molecular weights than 300 Da were found in the glyme permeate from the NF process, while predominantly higher molecular weight siloxanes were found in the NF retentate.

It should be noted that the embodiments and variations described herein are presented only as examples, and other variations in configuration and materials may be utilized while enjoying the benefits of the invention herein. Thus, the scope of the invention is to be measured by the allowed claims below rather than the embodiments described herein above.

What is claimed is:

1. A method of reducing organic contaminants in an effluent gas, the method comprising:
    directing the effluent through a liquid solvent comprising alkyl end-capped glymes to physically absorb the organic contaminants from the effluent, the solvent comprising one or more organic liquids having a molecular weight of less than 300, with inherent chemical stability towards catalysts, acids and bases;
    polymerizing the contaminants by directing them through a packed bed of catalyst media so as to create polymerized contaminants; and
    separating the polymerized contaminants from the solvent via filtration; and recycling the solvent for further physical absorption of incoming organic contaminants.

2. A method of reducing organic contaminants in an effluent gas, the method comprising:
    directing the effluent through a liquid solvent to physically absorb the organic contaminants from the effluent, the solvent comprising one or more organic liquids having a molecular weight of less than 300, with inherent chemical stability towards catalysts, acids and bases;
    polymerizing the contaminants by directing them through a packed bed of polymerization catalyst media so as to create polymerized contaminants, wherein the polymerization catalyst comprises the H-form of strongly acidic cationic ion-exchange resins; and
    separating the polymerized contaminants from the solvent via filtration; and
    recycling the solvent for further physical absorption of incoming organic contaminants.

3. The method of claim 2, wherein the polymerization catalyst comprises one or more of the following: a sulfonic or phosphonic acid polymeric bound resin; an alkyl or aryl sulfonic acid; an alkyl or aryl phosphonic acid; inorganic oxo-, halo-, or oxyhalo-acids, or other catalyst groups of similar functionality.

4. A method of reducing siloxane contamination in an effluent gas, the method comprising:
    directing the effluent through a reactor comprising a dialkyl terminated glyme solvent having a molecular size less than about 300 Daltons, the dialkyl terminated glyme serving to physically absorb the siloxanes from the effluent;

polymerizing the siloxanes by directing them through a packed bed of acidic resin catalyst media housed within the reactor and immersed within the solvent so as to create polymerized siloxanes having a molecular size greater than about 300 Daltons, that are soluble in the solvent; and separating the polymerized siloxanes from the solvent via nanofiltration; and recycling the solvent into the reactor for further physical absorption of incoming siloxanes.

* * * * *